(12) United States Patent
Skinner et al.

(10) Patent No.: US 11,707,608 B2
(45) Date of Patent: *Jul. 25, 2023

(54) PLEATED OR FOLDED CATHETER-MOUNTED BALLOON

(71) Applicant: Covidien LP, Mansfield, MA (US)

(72) Inventors: Dwight Skinner, Minneapolis, MN (US); Adam Tschida, Loretto, MN (US)

(73) Assignee: Covidien LP, Mansfield, MA (US)

( * ) Notice: Subject to any disclaimer, the term of this patent is extended or adjusted under 35 U.S.C. 154(b) by 173 days.

This patent is subject to a terminal disclaimer.

(21) Appl. No.: 17/239,017

(22) Filed: Apr. 23, 2021

(65) Prior Publication Data

US 2021/0236780 A1 Aug. 5, 2021

Related U.S. Application Data

(63) Continuation of application No. 14/484,784, filed on Sep. 12, 2014, now Pat. No. 10,987,494.

(Continued)

(51) Int. Cl.
*A61M 25/10* (2013.01)
*A61B 18/14* (2006.01)
(Continued)

(52) U.S. Cl.
CPC ..... *A61M 25/1002* (2013.01); *A61B 18/1492* (2013.01); *A61B 18/1815* (2013.01);
(Continued)

(58) Field of Classification Search
CPC ........ A61B 5/0422; A61B 2018/00029; A61B 2018/00166; A61B 2018/0022; A61B 2018/00238; A61B 2018/00267; A61B 2018/00375; A61B 2018/00577; A61B 2018/00839; A61B 2018/1407; A61B 2018/1435; A61B 2018/1467; A61B 2018/1475; A61B 18/1492; A61B 2090/3966; A61B 17/320068; A61B 18/1815; A61B 18/20; A61B 2018/00434; A61M 25/1002
(Continued)

(56) References Cited

U.S. PATENT DOCUMENTS 5,226,887 A * 7/1993 Farr .................. A61M 25/1027
604/103.09
5,871,483 A * 2/1999 Jackson ............. A61B 18/1492
606/41

(Continued)

*Primary Examiner* — Khadijeh A Vahdat
*Assistant Examiner* — Sean W Collins
(74) *Attorney, Agent, or Firm* — Shumaker & Sieffert, P.A.

(57) ABSTRACT

A catheter-mounted balloon includes an inflatable chamber defining a volume expandable from a deflated state to an inflated state, the inflatable chamber having a distal transition portion, a proximal transition portion, and a cylindrical body portion disposed between the distal transition portion and the proximal transition portion. The cylindrical body portion of the inflatable chamber includes a pleat zone having a pleat when the inflatable chamber is in the deflated state. The catheter-mounted balloon further includes an electrode disposed along a wall of the inflatable chamber. The pleat traverses the electrode such that is electrode is pleated as well.

26 Claims, 9 Drawing Sheets

Related U.S. Application Data

(60) Provisional application No. 61/877,923, filed on Sep. 13, 2013.

(51) Int. Cl.
*A61B 90/00* (2016.01)
*A61B 18/18* (2006.01)
*A61B 18/20* (2006.01)
*A61B 18/00* (2006.01)

(52) U.S. Cl.
CPC ....... *A61B 18/20* (2013.01); *A61B 2018/0022* (2013.01); *A61B 2018/00232* (2013.01); *A61B 2018/00238* (2013.01); *A61B 2018/00434* (2013.01); *A61B 2018/00577* (2013.01); *A61B 2018/1435* (2013.01); *A61B 2018/1465* (2013.01); *A61B 2090/3966* (2016.02); *A61B 2218/002* (2013.01); *A61M 2025/1004* (2013.01)

(58) Field of Classification Search
USPC .......................................................... 606/41
See application file for complete search history.

(56) References Cited

U.S. PATENT DOCUMENTS

| | | | |
|---|---|---|---|
| 10,987,494 B2* | 4/2021 | Skinner | A61B 18/1492 |
| 2007/0016278 A1* | 1/2007 | Shippy, III | A61M 25/1038 |
| | | | 604/103.08 |

* cited by examiner

PLEATED OR FOLDED CATHETER-MOUNTED BALLOON

CROSS REFERENCE TO RELATED APPLICATIONS

This application is a continuation of U.S. application Ser. No. 14/484,784, filed Sep. 12, 2014, and entitled, "PLEATED OR FOLDED CATHETER-MOUNTED BALLOON," which claims priority to U.S. Provisional Application Ser. No. 61/877,923, filed on Sep. 13, 2013, entitled "A Pleated or Folded Catheter-Mounted Balloon," which are hereby incorporated herein by reference in their entirety.

This application is related to the following patents or patent applications, each of which is hereby incorporated herein by reference in its entirety: PCT/US2012/057967, filed on Sep. 28, 2012, U.S. Provisional Application Ser. No. 61/541,765, filed on Sep. 30, 2011, U.S. Provisional Application Ser. No. 61/593,147, filed on Jan. 31, 2012, U.S. Provisional Application Ser. No. 61/113,228, filed Dec. 11, 2008; U.S. Provisional Application Ser. No. 61/160,204, filed Mar. 13, 2009; U.S. Provisional Application Ser. No. 61/179,654, filed May 19, 2009; U.S. Patent Application Publication No. 2010/0204560, filed Nov. 11, 2009; U.S. Provisional Application Ser. No. 61/334,154, filed May 12, 2010; and U.S. patent application Ser. No. 13/106,658, filed May 12, 2011.

BACKGROUND

Hypertension and other related cardiovascular disorders are major health concerns affecting many adults in the developed world. These conditions can be especially severe for patients with so-called drug-resistant hypertension (e.g., those unable to achieve target blood-pressure values despite multiple drug therapies at their proper doses). Renal denervation may be used for the treatment of hypertension, cardiovascular disorders, chronic renal diseases, or other related diseases or disease states. It is believed renal denervation has an impact on sympathetic renal nerve activity.

Renal denervation can be performed using minimally invasive procedures that use balloon-mounted catheters to navigate through blood vessels to deliver treatment to target sites in the blood vessel. Conventional catheters have balloons that "bunch up" when pulled or forced through the catheter body, often forming tight random non-deterministic folds. This makes insertion through the guide catheter and pull-back into the guide catheter difficult as the nature of the folds greatly increases the force required to insert or withdraw the balloon catheter.

SUMMARY

This disclosure describes systems and methods for pleating a catheter-mounted balloon (e.g., by thermal, mechanical, or chemical means), such that the balloon preferentially folds in a predictable pattern along the pleat lines when collapsed and pushed through the catheter. By fabricating the balloon to fold automatically according to pre-determined pleat patterns, the force required to insert or withdraw the balloon can be greatly reduced, as compared to a non-pleated balloon, thus lowering the forces required to insert or withdraw a balloon catheter. Additionally or alternatively, the pleats may be configured such that inflation of the balloon requires less pressure than in a typical system, for example, by using looser pleats than in balloons without pre-pleating. The pre-pleating may also permit use of a smaller catheter in some cases. For ease of illustration, embodiments are discussed in the context of devices, methods, and systems for achieving renal denervation for the treatment of hypertension, other cardiovascular disorders, and chronic renal diseases. Illustrative embodiments are described in the context of using energy-based devices (e.g., radio-frequency based devices) and methods to reduce renal sympathetic activity in the renal nerves without causing damage to non-target cells. However, the embodiments may be adapted and applied in other types of applications, including other neuromodulation devices, without departing from the scope of the disclosure.

The systems, devices, and methods described herein can be used to affect neural communication to and from the one or both kidneys to improve cardio-renal function of the patient, such that the kidney continues to function in the patient. Thus, renal nerve fibers can be deactivated (permanently or temporarily) without being completely physically severed (e.g., without fully cutting).

In one aspect, a catheter-mounted balloon includes an inflatable chamber defining a volume expandable from a deflated state to an inflated state, the inflatable chamber having a distal transition portion, a proximal transition portion, and a cylindrical body portion disposed between the distal transition portion and the proximal transition portion. The cylindrical body portion of the inflatable chamber includes a pleat zone having a pleat when the inflatable chamber is in the deflated state. The catheter-mounted balloon further includes an electrode disposed along a wall of the inflatable chamber. The pleat traverses the electrode such that the electrode is pleated as well. In one example, the electrode may be helical around a longitudinal axis of the inflatable chamber.

According to some implementations, the inflatable chamber defines at least one irrigation aperture to allow fluid to flow from within the balloon to outside the balloon when the balloon is in the inflated state. The irrigation aperture is at least partially unobstructed by the pleat when the inflatable chamber is in the deflated state. By avoiding complete obstruction of the pleat, these embodiments may reduce the likelihood of damage to the irrigation aperture shapes and may facilitate providing irrigation for the balloon even when the balloon is not fully inflated. In one example, the at least one irrigation aperture is disposed between the pleat and a side of the electrode.

According to some implementations, the pleat zone having the pleat defines an opening between a first side of the pleat and a second side of the pleat when the inflatable chamber is in the deflated state. Such an opening can reduce the likelihood of pleating the inflatable chamber tightly to the point of damaging the material of the inflatable chamber, damaging any electrode pleated along with the inflatable chamber, or requiring excessive application of pressure to unfold and inflate the inflatable chamber.

In some implementations, the pleat extends at least partially into the proximal transition portion of the inflatable chamber. For example, at least a portion of the pleat can be substantially parallel to a longitudinal axis of the cylindrical body portion of the inflatable chamber when the inflatable chamber is in the deflated state. Additionally or alternatively, at least a portion of the pleat can be a spiral around the longitudinal axis of the cylindrical body portion when the inflatable chamber is in the deflated state. Additionally or alternatively, at least a portion of the pleat is a substantially zig-zag pattern along the longitudinal axis of the cylindrical body portion when the inflatable chamber is in the deflated state. As yet another additional or alternative example, at least a portion of the pleat is substantially parallel to an edge of the electrode.

The inflatable chamber may be collapsible along the pleat in response to a decrease in the volume of the inflatable chamber as the inflatable chamber is deflated from the inflated state to the deflated state.

In certain implementations, the diameter of the cylindrical body portion of the inflatable chamber is in any of the ranges between about 0.01 inches and about 0.03 inches, between about 0.01 inches and about 0.015 inches, or between about 0.015 inches and about 0.019 inches, when the inflatable chamber is in the deflated state. In certain implementations, the diameter of the cylindrical body portion of the inflatable may be less than about 0.01 inches when the inflatable chamber is in the deflated state.

According to another aspect, a catheter includes a pleated catheter-mounted balloon as described herein, and a guidewire for delivering the catheter-mounted balloon to an intravascular treatment site, while the inflatable chamber of the delivered catheter-mounted balloon is in the deflated state.

In yet another aspect, an energy-based system is provided. The system comprises a nerve modulation device including a balloon as described herein positioned in a vicinity of neural fibers that innervate a kidney of a patient, where the energy-based device is configured to alter neural communication to and from the kidney.

In yet another aspect, a method is provided for performing a renal neuromodulation procedure to treat a heat-related condition using a catheter-mounted balloon, a catheter, or a energy-based system as described herein.

This description may use the phrases "in embodiments," "in some embodiments," or "in certain embodiments," which may each refer to one or more of the same or different embodiments in accordance with the present disclosure.

As used herein, the terms proximal and distal include a direction or a position along a longitudinal axis of a catheter or medical instrument. The term "proximal" includes the end of the catheter or medical instrument closer to the operator, while the term "distal" includes the end of the catheter or medical instrument closer to the patient. For example, a first point is proximal to a second point if it is closer to the operator end of the catheter or medical instrument than the second point. The term "operator" includes any medical professional (e.g., doctor, surgeon, nurse, or the like) performing a medical procedure involving the use of aspects of the present disclosure described herein.

Embodiments can include one or more of the following advantages.

A balloon that is fabricated to fold according to pre-determined pleat patterns can be designed to fold into a substantially uniform tubular shape, which can lead to a reduction in the force required to insert or withdraw the balloon. The tightness of pleats can be arranged to allow a pleat to retain an opening between its two sides when the balloon is deflated, and by so doing, reduce the pressure required for inflating the balloon below that required for balloons with tighter pleats. Compared with unpleated balloons, balloons pleated to fold in a preferential configuration can be compatible with a wider range of guide catheters having smaller inner diameters and less lubricious inner catheter surfaces, resulting in smaller punctures during minimal-invasive surgery and shorter recovery times.

BRIEF DESCRIPTION OF THE DRAWINGS

The foregoing and other objects and advantages will be apparent upon consideration of the following detailed description, taken in conjunction with the accompanying drawings, in which like reference characters refer to like parts throughout, and in which.

DETAILED DESCRIPTION

To provide an overall understanding of the systems, devices, and methods described herein, particular embodiments of the present disclosure are described herein with reference to the accompanying drawings. However, the disclosed embodiments are merely examples of the disclosure and may be embodied in various forms.

Figure 1A:
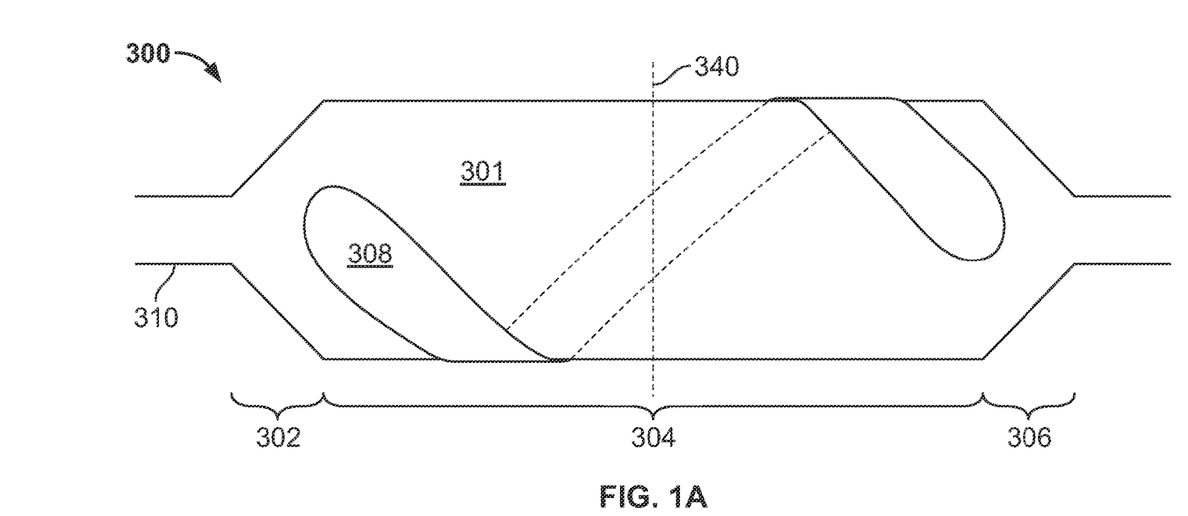
FIG. 1A is a side view of an illustrative catheter-mounted balloon.
Figure 1B:
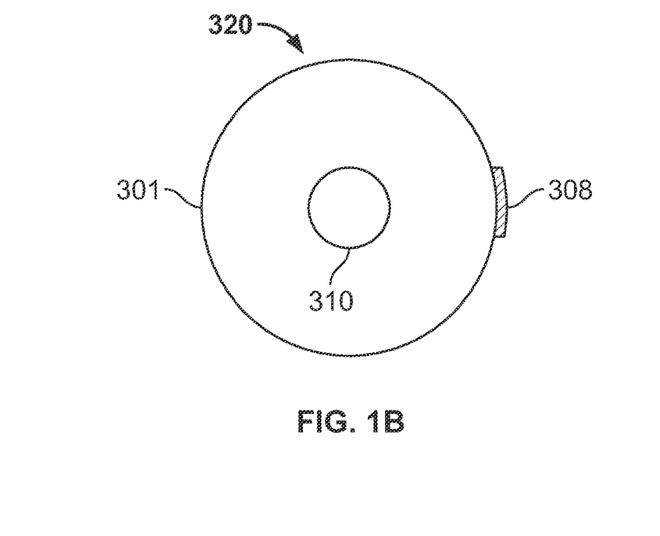
FIG. 1B is a cross-section of the balloon in FIG. 1A when the catheter-mounted balloon is in the inflated state.
Figure 1C:
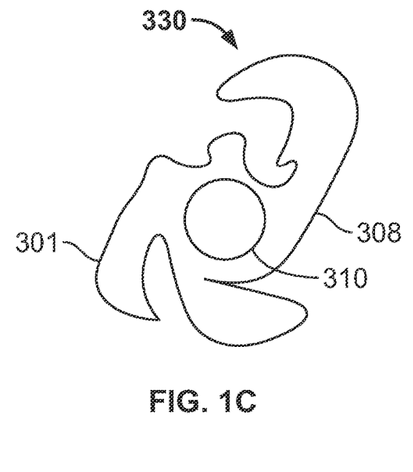
FIG. 1C is a cross-section of the balloon in FIG. 1A when the catheter-mounted balloon is in the deflated state.

FIG. 1A is a side view of a catheter-mounted balloon 300 without pleats. Balloon 300 is shown in an inflated state, secured to an elongate member (which may be a catheter shaft) 310. FIG. 1B is a corresponding cross-section 320 of balloon 300 when balloon 300 is expanded or in an inflated state, and FIG. 1C is a cross-section 330 of balloon 300 when balloon 300 is collapsed or in a deflated state. Cross-sections 320 and 330 are taken at the anterior-posterior axis 340 shown in FIG. 1A.

Balloon 300 includes an inflatable chamber 301 defining a volume expandable from a deflated state to an inflated state, and one or more electrodes 308 for providing treatment intravascularly to various treatment sites, including for providing an energy signal to renal nerves within the renal artery to achieve renal denervation. In the example of balloon 300, the electrode 308 is a single helical electrode disposed on a wall of the balloon. However, any suitable electrode, including any non-helical electrode (e.g., a point-by-point electrode), may be used. In some embodiments, the electrode 308 is a rigid electrode that does not fold along with the balloon.

Inflatable chamber 301 includes a distal transition portion 302, a cylindrical body portion 304, and a proximal transition portion 306. Distal transition portion 302 and proximal transition portion 306 are frustoconical shapes that taper inwardly away from cylindrical body portion 304. In this embodiment, electrode 308 is in a helical or spiral configuration around a longitudinal axis of cylindrical body portion 302 of inflatable chamber 301. The helical shape of electrode 308 can increase the likelihood of delivery of RF energy to nerves that are not uniformly distributed around a circumference of a renal artery. It should be appreciated, however, that without departing from the scope of the present disclosure, electrode 308 may take on any suitable shape or configuration. Additionally or alternatively, more than one electrode may be disposed on the inflatable chamber 301.

Electrode 308 delivers energy to a tissue or vascular region when inflatable chamber 301 is in the inflated state and in contact with or is nearly in contact with the tissue or vascular region. In some embodiments, at least one irrigation aperture (not shown in FIGS. 1A-1C) is defined by cylindrical body portion 302 to facilitate fluid flow from within inflatable chamber 301 to outside inflatable chamber 301 when inflatable chamber 301 is in the inflated state. Irrigation through one or more irrigation apertures can provide cooling of the wall of inflatable chamber 301, electrode 308, and/or tissue in the vicinity of the electrode 308 during treatment.

In general, balloon 300 is delivered through a guide catheter (not shown) to a vessel such as a renal artery, where balloon 300 is pushed out from the guide catheter to be placed in proximity to a vascular wall at a treatment site. Once balloon 300 is in position, fluid is pumped from a reservoir (not shown) into inflatable chamber 301 from proximal transition portion 306 in a closed loop or an open loop configuration. For example, saline may be pumped under constant flow through an irrigation lumen (not shown) to cause inflatable chamber 301 to expand or inflate until an external wall (or a portion thereof) of inflatable chamber 301 makes contact with an inner wall of the vessel. Once fully inflated, inflatable chamber 301 may assume the shape of cross-section 320 shown in FIG. 1B, and electrode 308 on the inflatable chamber 301 may assume the helical configuration shown in FIG. 1A. Energy is delivered to electrode 308, which may be coupled to a conductive guide wire (not shown). Once the energy delivery process terminates, fluid flow is stopped, and inflatable chamber 301 collapses into the deflated state. Deflated balloon 300 is then pulled back into the catheter and retrieved from the treatment site.

FIG. 1C shows an example of a cross-section 330 of balloon 300, when balloon 300 is in a deflated or collapsed state, for example, when forced through a guide catheter. It should be appreciated that, without pleats to guide preferential folding of balloon 300, the cross-section 330 shown in FIG. 1C is illustrative, as the cross-section 300 may vary considerably each time the balloon 300 is in the deflated or collapsed state. As fully or partially deflated balloon 300 is pushed or pulled through the guide catheter, depending on the shape of inflatable chamber 301, and material properties of inflatable chamber 301 and electrode 308, balloon 300 may tightly or loosely fold onto itself and "bunch up," thus requiring a large force to insert or withdraw the balloon 300 relative to the guide catheter. During balloon deployment, the distal end of the guide catheter may be protected with a silicon seal that provides additional resistance to movement of the balloon.

To exert more control over the shape and configuration of balloon 300 in a fully or partially deflated state so balloon 300 may more easily move out of and into a guide catheter, pleating (e.g., thermal pleating) may be applied to balloon 300 during the manufacturing process, such that balloon 300 folds in preferential configurations when pushed through the guide catheter, and collapses in similar preferential configurations when pulled back into the guide catheter. By pleating and allowing balloon 300 to fold according to pre-determined pleat patterns, the force required to insert or withdraw the balloon through the catheter can be greatly reduced, thus facilitating successful deployment of balloon 300.

Inflatable chamber 301 may comprise a layer of shape memory material such as shape-memory polymers which can retain or recover different shapes and can transition easily between those shapes with minimal force. Such shape restoration properties help retain preferential shape configuration after inflation of balloon 300 and subsequent deflation processes. Examples of shape memory materials include polyurethane-based shape memory polymers, and polyether foams.

Figure 2A:
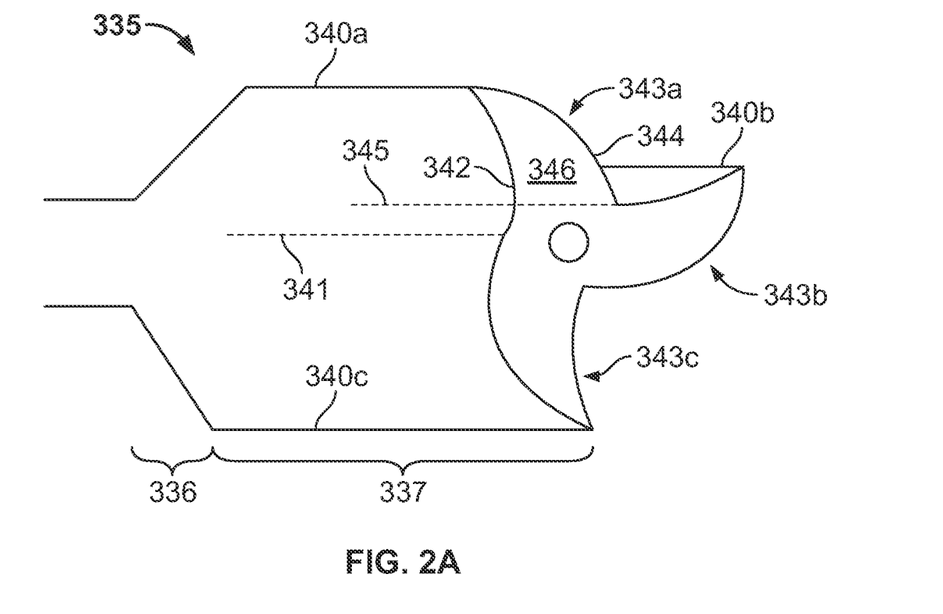
FIG. 2A is a perspective cross-section view of an inflatable chamber of a catheter-mounted balloon with three pleat zones.
Figure 2B:
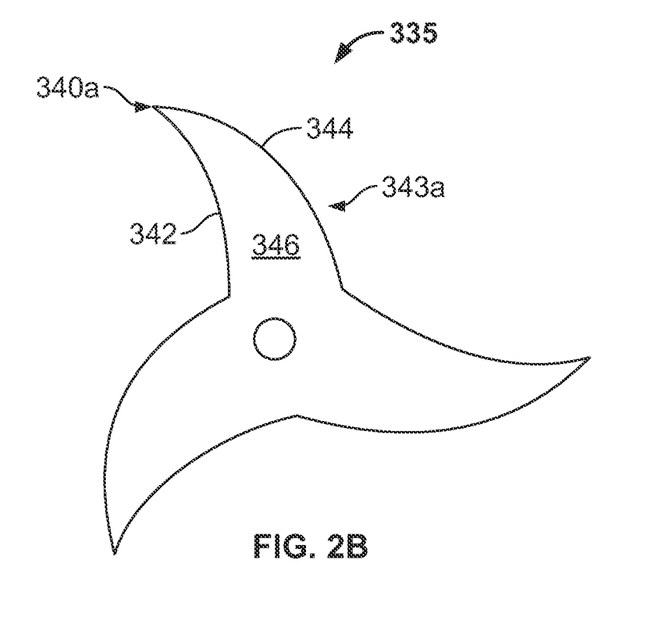
FIG. 2B is a cross-section of the inflatable chamber in FIG. 2A.

FIG. 2A is a perspective cross-section of an illustrative pleated inflatable chamber 335, which includes a proximal transition portion 336 and a cylindrical body portion 337. Inflatable chamber 335 can be used, for example, in place of inflatable chamber 301 in FIG. 1A. For clarity of illustration, only a fraction of cylindrical body portion 337 is shown in FIG. 2A. FIG. 2B shows a corresponding cross-sectional view of the inflatable chamber 335 in FIG. 2A. In both figures, pleated inflatable chamber 335 is in a deflated or partially deflated state. Cylindrical body portion 337 includes three longitudinal pleats 340a, 340b and 340c. As used herein, a "pleat" includes a fold or a bend of a surface, and a "pleat zone" includes a portion of the surface that includes the pleat. For example, pleat 340a is included in pleat zone 343a bordered by folds 341 and 345. Pleat zone 343a includes pleat 340a as well as a first side 342 of pleat 340a and a second side 344 of pleat 340a. In some embodiments, inflatable chamber 301 is collapsible along the pleats in response to a decrease in the volume of inflatable chamber 301 as inflatable chamber 301 is deflated from the inflated state to the deflated state.

In the pleated inflatable chamber 335 shown in FIG. 2A, pleat zone 343a defines an opening 346 between first side 342 of pleat 343a and second side 344 of pleat 343a when the balloon is in a fully or partially deflated state. A loose pleat in a pleat zone with an opening (e.g., pleat zone 343a with opening 346) allows the application of a lower fluid pressure when a catheter-mounted balloon is inflated. For example, a loosely pleated balloon may be properly inflated when the fluid pressure is in the range from about 5 psi to about 100 psi, or from 10 psi to 50 psi, while a tightly pleated balloon (e.g., a balloon pleated with two-layer gaps) may require a fluid pressure in the range from about 100 psi to about 400 psi. Additionally or alternatively, loose pleating can reduce the likelihood of damage to the mechanical integrity of the balloon.

In addition, depending on the material composition of inflatable chamber 335, the manufacturing process which may involve thermal treatment, and the operational pressure of the inflatable chamber 335, pleats 340a, 340b, 340c within inflatable chamber 335 may maintain their shape within the normal operational pressure range of the inflatable chamber 335. In other words, the pleats 340a, 340b, 340c can self-recover and fold back into a preferential configuration to facilitate the retrieval of the balloon 300 back into the guide catheter.

As compared to a balloon without pleats, pleating of inflatable chamber 335 of balloon 300 reduces the circumferential length of the inflatable chamber 335 when the inflatable chamber 335 is in a fully or partially deflated state. This reduced circumferential length can facilitate, for example, the use of smaller diameter guide catheters which can be accommodated by smaller punctures during minimally invasive surgery, and consequently can reduce patient recovery time. In some embodiments, the diameter of a pleated cylindrical body portion 337 of inflatable chamber 335 is less than about 0.025 inch when inflatable chamber 335 is in the deflated state. In certain embodiments, the diameter of pleated cylindrical body portion 337 of inflatable chamber 335 is less than about 0.019 inch when inflatable chamber 335 is in the deflated state. In some embodiments, the diameter of pleated cylindrical body portion 337 of inflatable chamber 335 is in any of the ranges between about 0.01 inches and about 0.015 inches, between about 0.01 inch and 0.03 inches, between about 0.015 inches and about 0.019 inches when the inflatable chamber is in the deflated state. In some embodiments, the diameter of pleated cylindrical body portion 337 of inflatable chamber 335 is less than about 0.01 inch when inflatable chamber 335 is in the deflated state.

Pleats 343a, 343b, and 343c are sharp folds that can be viewed as the intersecting line between two surfaces. In some embodiments, pleats 343a, 343b, and 343c may be soft, with substantially round corners that can bend and fold into a predetermined configuration. Soft pleats are advantageous, for example, in embodiments wherein one or more pleats 343a, 343b, 343c traverse an electrode (e.g., electrode 118 in FIG. 1A) such that the electrode is pleated. For example, as compared to sharp pleats, soft pleats may be useful for reducing the likelihood that electrical properties of the traversed electrode will be compromised by the pleat while still facilitating the use of reduced force to insert and withdraw a balloon within a guide catheter.

Although three pleats are shown in FIGS. 2A and 2B, in various embodiments, a catheter-mounted balloon may include any suitable number of pleats, pleat shapes, pleat sizes, and pleat patterns.

FIGS. 3-7 are cross-sections of exemplary pleated inflatable chambers, with each inflatable chambers shown in a deflated state.

Figure 3:
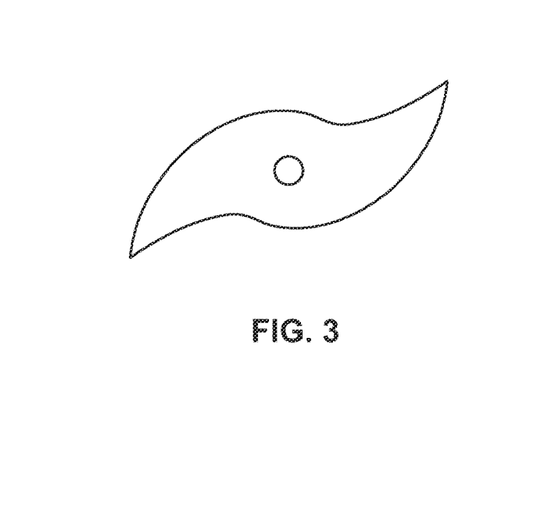
FIGS. 3 to 7 are cross-sections of example catheter-mounted balloons with pleats.

FIG. 3 is a cross-sectional view of an inflatable chamber with two radially symmetrical pleats, which may facilitate rotation of a catheter-mounted balloon through a guide catheter (e.g., a guide catheter having a lubricious inner surface and/or a guide catheter having grooves complementary to the pleat pattern). In the examples shown in FIGS. 2A and 2B, pleats extend longitudinally across the cylindrical body portion 337. In some embodiments, however, the pleats may be a spiral around the longitudinal axis of the inflatable chamber when the inflatable chamber is in a fully or partially deflated state, and/or may form a substantially zig-zag pattern along the longitudinal axis of the cylindrical body portion when the inflatable chamber is in the deflated state.

Figure 4:
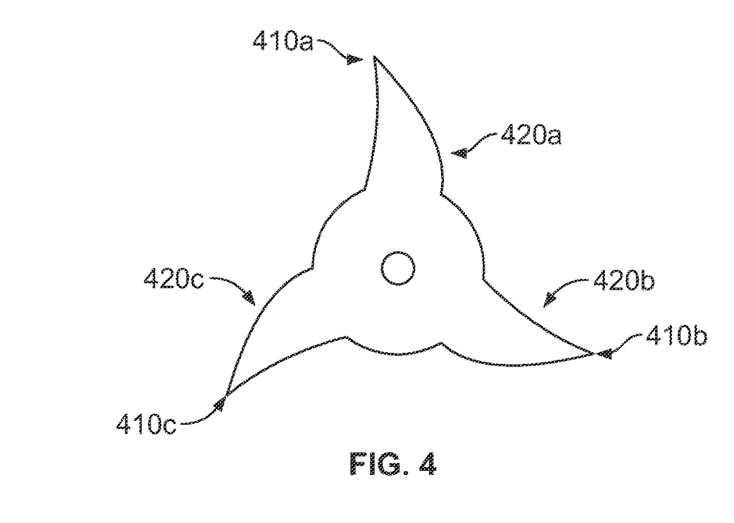

FIG. 4 is a cross-sectional view of an inflatable chamber with three radially symmetrical pleats. As compared to pleats 340a, 340b, and 340c in FIGS. 2A and 2B which are in adjacent pleat zones, pleats 410a, 410b, and 410c shown in FIG. 4 are located in respective pleat zones 420a, 420b, and 420c spaced apart on the surface of the inflatable chamber.

Figure 5:
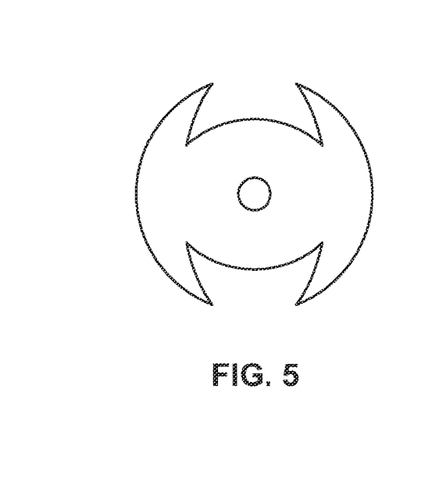

FIG. 5 is a cross-sectional view of an inflatable chamber with four pleats, where the orientation of the pleats is configured so the circumferential shape of the inflatable chamber is circular.

Figure 6:
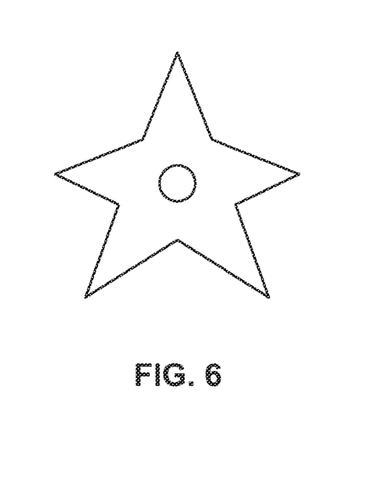

FIG. 6 is a cross-sectional view of an inflatable chamber with five pleats. In general, any suitable number of pleats may be set (e.g., thermally set) into the inflatable chamber of a catheter-mounted balloon.

Figure 7:
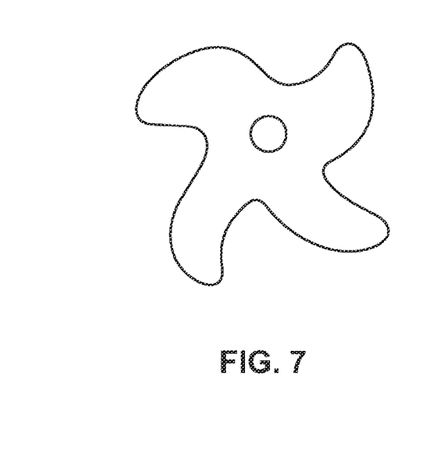

FIG. 7 illustrates an inflatable chamber with four soft pleats. As described herein, soft pleats may be used when a pleat traverses an electrode disposed on the inflatable chamber, where traversal of the electrode by the pleat causes the electrode to be pleated as well and, as compared to a sharp pleat, the soft pleat is less likely to impact the electrical properties and/or structural integrity of the electrode.

FIGS. 8-11 are side views of example pleating patterns of pleated balloons, each balloon including one or more pleats, one or more electrodes and, optionally, defining one or more irrigation apertures.

Figure 8:
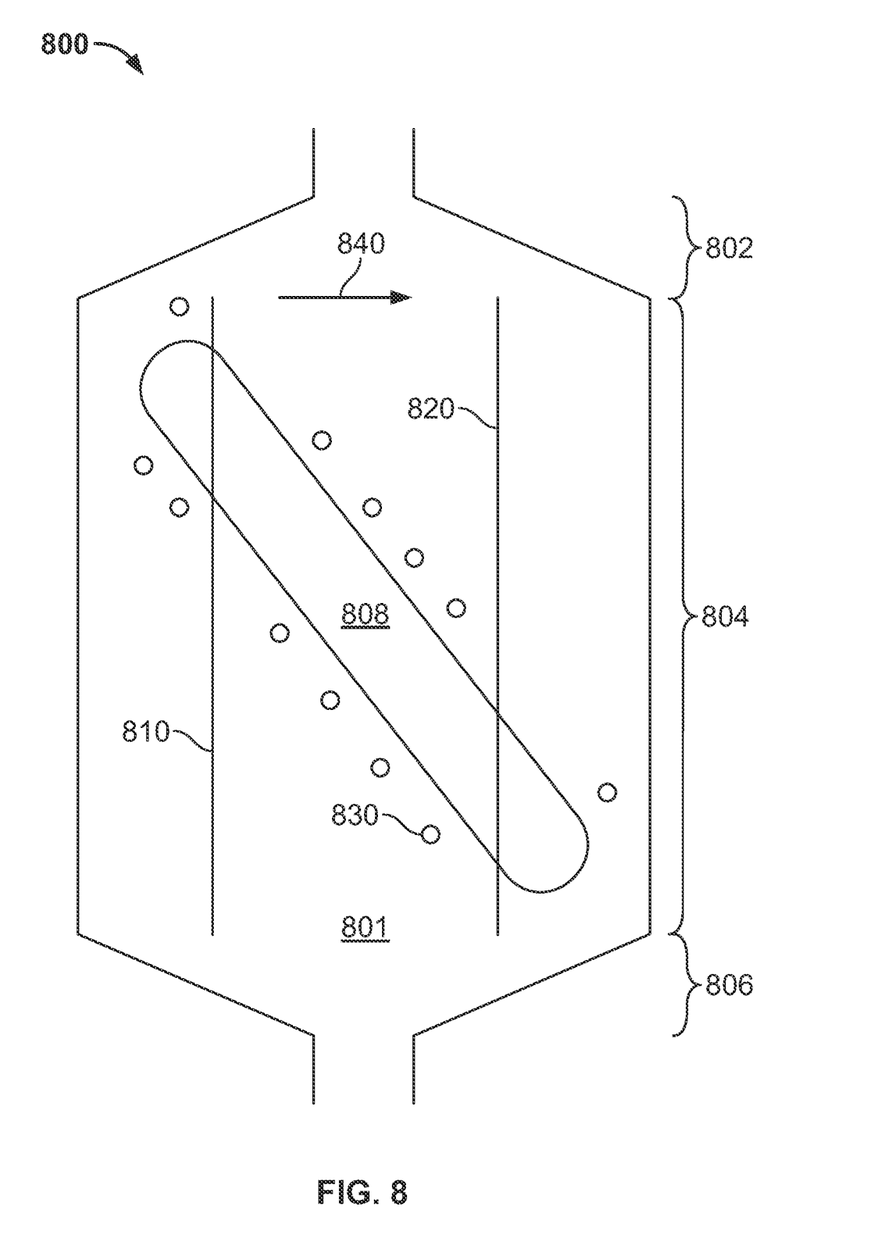
FIGS. 8 to 11 are side views of example plating patterns of catheter-mounted balloons with pleats.

Referring to FIG. 8, a balloon 800 includes an inflatable chamber 801 and an electrode 808, with electrode 808 disposed (e.g., diagonally disposed) on inflatable chamber 801. In the illustrated example, inflatable chamber 801 includes two pleats 810 and 820, each of which extends across electrode 808. It should be appreciated, however, one of pleats 810 and 820 can be arranged to extend across electrode 808 while the other of pleats 810 and 820 does not extend across electrode 808. Additionally or alternatively, it should be appreciated that inflatable chamber 801 can includes fewer or greater pleats without departing from the scope of the present disclosure.

In the deflated state, the cross-section of inflatable chamber 801 may be as shown in FIG. 3. Inflatable chamber 801 includes a proximal transition portion 802, a cylindrical body portion 804, and a distal transition portion 806. In this example, pleats 810 and 820 extend longitudinally along cylindrical body portion 804, from proximal transition portion 802 to distal transition portion 806.

In this example, irrigation apertures 830 flank both sides of electrode 808 to cool the electrode during energy delivery. In some embodiments, irrigation apertures 830 are placed and designed so that, in a fully or partially deflated state of inflatable chamber 801, pleats 810 and 820 do not fully obstruct irrigation apertures 830 and, thus, do not entirely block fluid flow through irrigation apertures 830, reducing the likelihood of pressure buildup within inflatable chamber 801. In some embodiments, irrigation apertures 830 may be partially blocked by a pleat when the inflation chamber 801 is in the deflated state.

Pleats 810 and 820 may fold in pre-determined directions. In this example, pleat 810 and pleat 820 may fold to the right, in direction 840, and no irrigation apertures are disposed immediately next to pleats 810 and 820.

Figure 9:
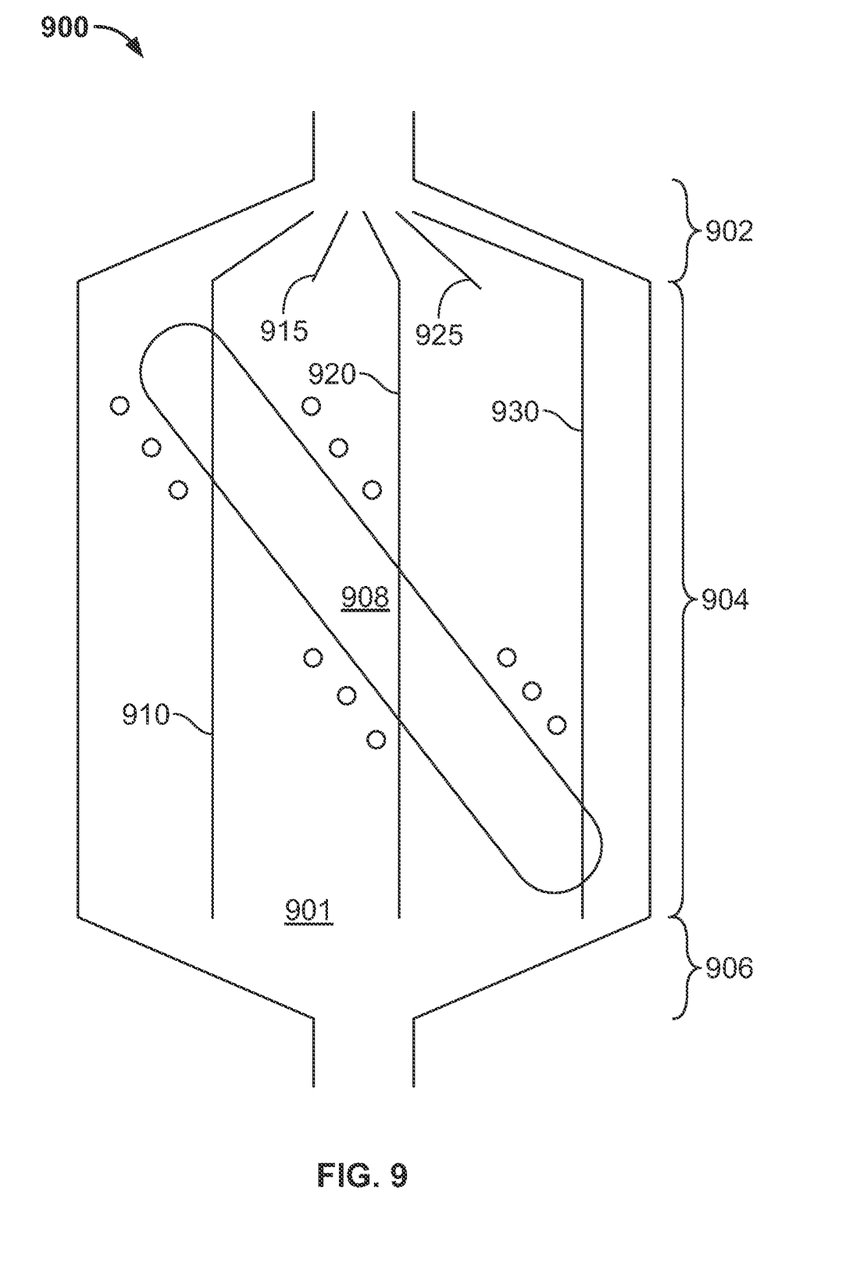

Referring to FIG. 9, a balloon 900 includes an inflatable chamber 901 and an electrode 908. Inflatable chamber 901 includes three pleats 910, 920, and 930, and electrode 908 is disposed on inflatable chamber 901 such that each pleat 910, 920, and 930 extends across electrode 908. In a fully or partially deflated state, the cross-section of inflatable chamber 901 may be as shown in FIG. 2B or FIG. 3. In the example shown in FIG. 9, pleats 910, 920, and 930 extend longitudinally along the cylindrical body portion 904 and also into proximal transition portion 902 of inflatable chamber 901. The full or partial extension of pleats 910, 920, and 930 into proximal transition portion 902 may facilitate winding of inflatable chamber 901 and electrode 908 when balloon 900 is pulled back into a guide catheter after energy delivery. Additionally or alternatively, pleats 815 and 825 may be included in proximal portion 902 to facilitate the folding of balloon 900. Additionally or alternatively, one or more pleats may extend into distal portion 906.

Figure 10:
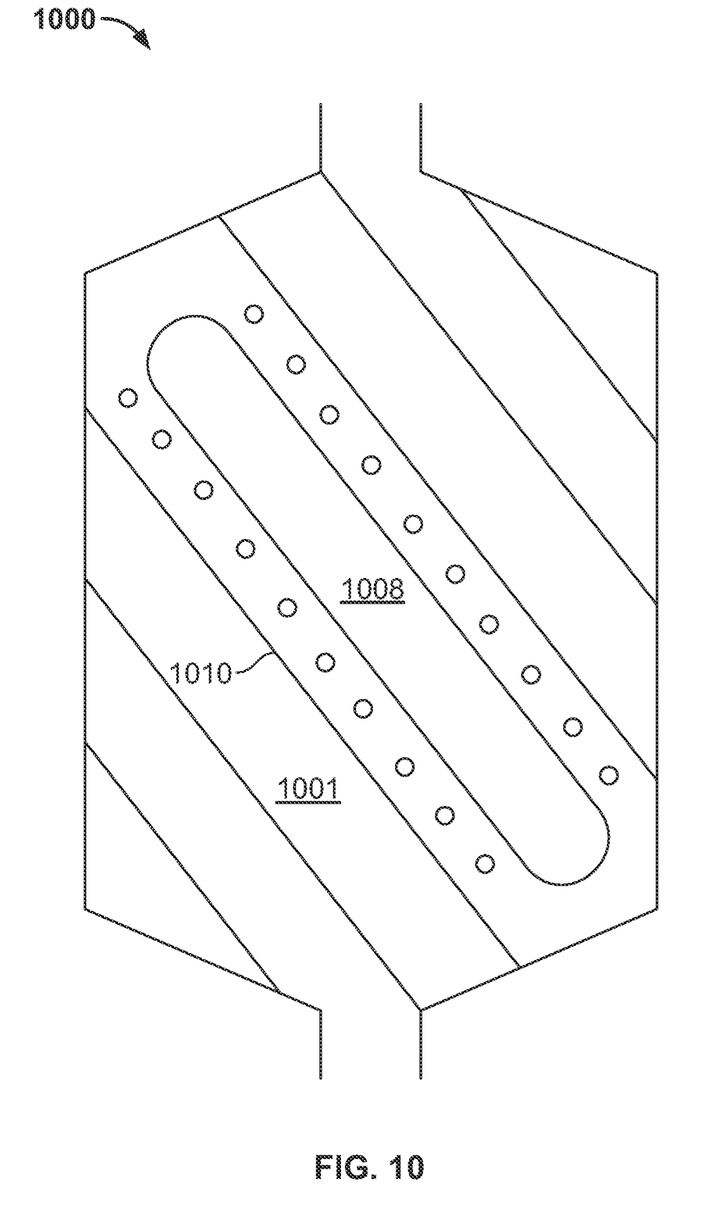

Referring now to FIG. 10, a balloon 1000 includes an inflatable chamber 1001 and an electrode 1008. Inflatable chamber 1001 includes six pleats 1010, and electrode 1008 is disposed on inflatable chamber 1001 such that pleats 1010 do not cross electrode 1008. Pleats 1010 and, optionally, irrigation apertures flank both sides of electrode 1008.

Figure 11:
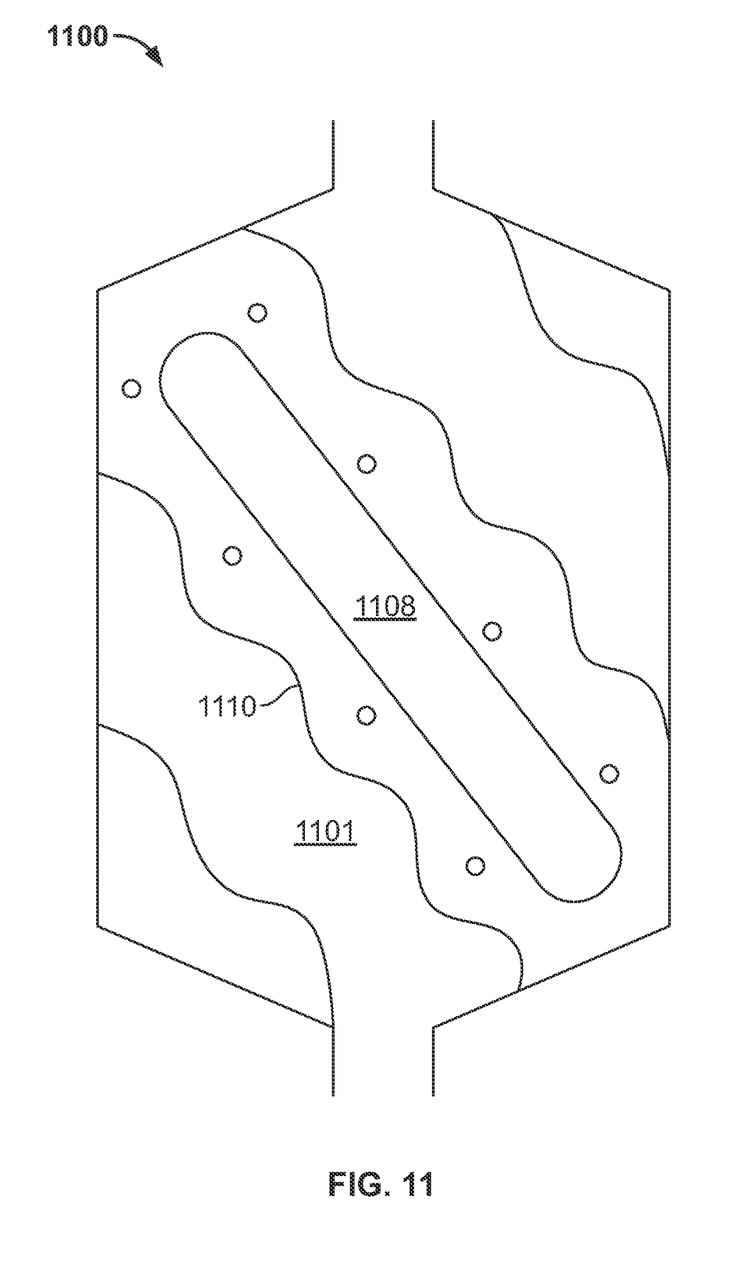

Referring to FIG. 11, a balloon 1100 includes an inflatable chamber 1101 and an electrode 1108. Inflatable chamber 1101 includes four crinkled pleats 1110, and electrode 1108 is disposed on inflatable chamber 1101 such that pleats 1110 flank both sides of electrode 1108. In certain embodiments, inflatable chamber 1101 defines irrigation apertures. In some embodiments, at least a portion of each pleat 1110 is a substantially zig-zag pattern along the longitudinal axis of a cylindrical body portion of inflatable chamber 1101 when inflatable chamber 1101 is in the deflated state. In certain embodiments, at least a portion of one pleat 1110 is a spiral around a longitudinal axis of the cylindrical body portion when inflatable chamber 1101 is in the deflated state. In general, any suitable number of irrigation apertures may be included, at any reasonable positions and pleats 110 may be folded in different orientations to avoid blocking the irrigation apertures during fluid flow.

The systems, devices, methods, electrodes, inflatable chambers, and balloons described above may be incorporated into a system to provide, for example, renal denervation treatment.

Figure 12A:
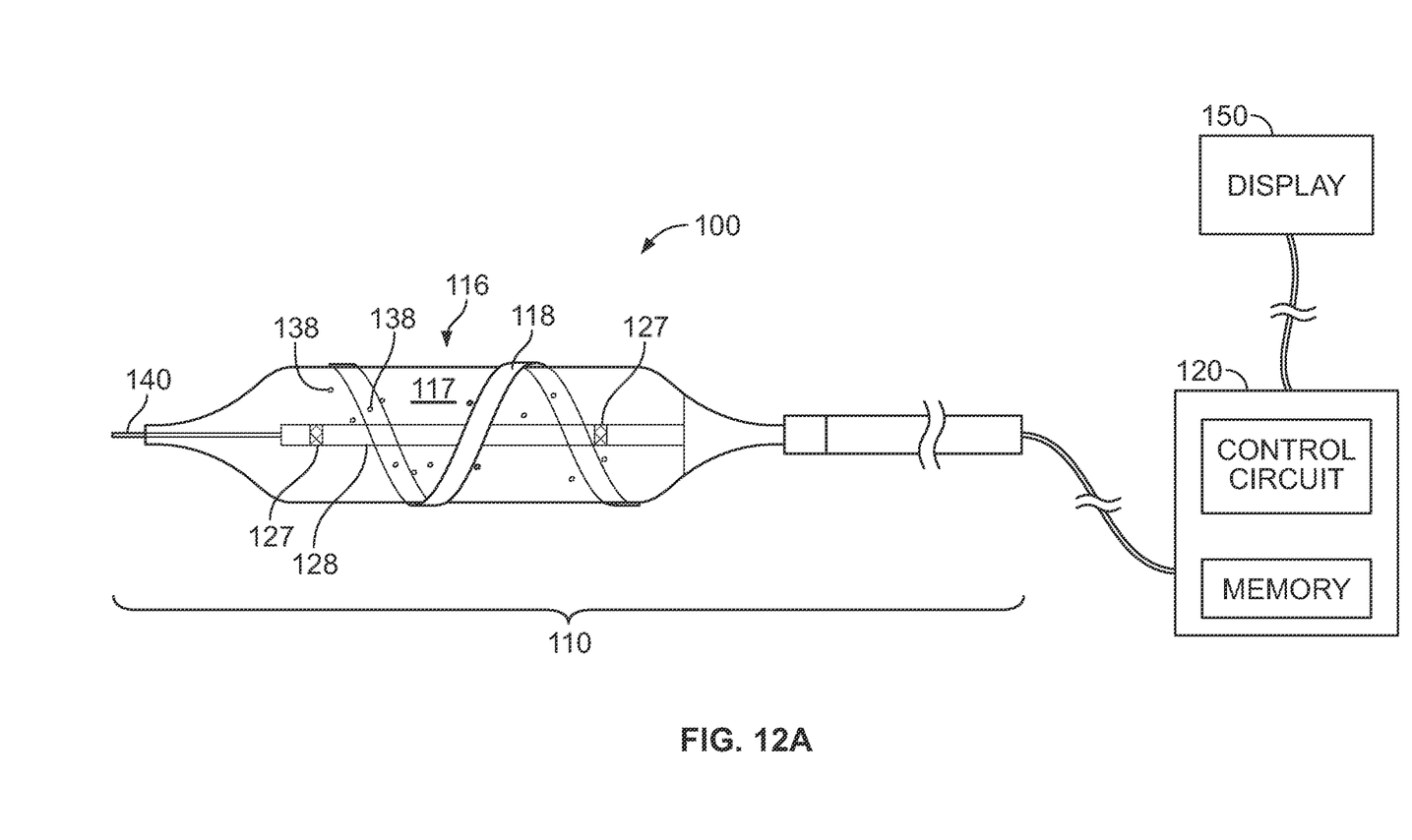
FIG. 12A is a schematic representation of an energy-delivery system for providing renal neuromodulation according to some embodiments.

FIG. 12A illustrates an energy-delivery system 100 for providing renal neuromodulation according to some embodiments. The system 100 includes an energy delivery device 110, energy generator 120, and display 150. The energy delivery device 110 can be, for example, any of the energy delivery devices described herein. In the example of system 100, the energy-delivery device 110 is a balloon catheter sized for intravascular placement to deliver energy to neural fibers along a renal artery to modulate sympathetic renal nerve activity.

The system 100 includes a user interface device 150 for communicating input and output information to the operator of the system. In some embodiments, the user interface device 150 is a display device. The display can be, for example, a touch screen interface for user input, and can display instructional messages and procedural feedback, such as power delivered, impedance, and remaining treatment time. In some embodiments, the user interface device 150 communicates to the operator warning messages.

The system 100 includes energy generator 120 which provides an energy signal the energy delivery device 110. The energy generator 120 includes control circuitry and memory for controlling the operation of the system. The energy generator 120 can be coupled to the energy delivery device (and/or to the user interface device 150) by wired or wireless link. In this example, the energy generator 120 is placed external to the patient.

Although shown separately from the user interface device 150, the energy generator 120 may be integrated with the user interface device 150 in a single housing. In some embodiments, the energy generator 120 includes memory, processing circuitry, firmware, and hardware for programming or controlling the system 100 to provide treatment to tissue. The energy generator 120 can provide any suitable type of energy signal to the energy delivery device 110. In some embodiments, renal neuromodulation may be achieved via generation and/or application of thermal energy to the target neural fibers, such as through application of a an energy field, including, electromagnetic energy, radio frequency, ultrasound (including high-intensity focused ultrasound), microwave, light energy (including laser, infrared and near-infrared) etc., to the target neural fibers. For example, thermally-induced renal neuromodulation may be achieved via delivery of a pulsed or continuous thermal energy field to the target neural fibers. The energy field can be sufficient magnitude and/or duration to thermally induce the neuromodulation in the target fibers (e.g., to heat or thermally ablate or necrose the fibers).

Without wishing to be bound by theory, it is believed that thermal ablation or non-ablative alteration of the target neural fiber at least partially denervates the kidney innervated by the neural fibers via heating. Thermal heating mechanisms for neuromodulation include both thermal ablation and non-ablative thermal alteration or damage (e.g., via sustained heating or resistive heating). Thermal heating mechanisms may include raising the temperature of target neural fibers above a desired threshold to achieve non-ablative thermal alteration, or above a higher temperature to achieve ablative thermal alteration. For example, the target temperature can be above body temperature (e.g., approximately 37 degrees C.) but less than about 45 degrees C. for non-ablative thermal alteration, or the target temperature can be about 45 degrees C. or higher for the ablative thermal alteration. The length of exposure to thermal stimuli may be specified to affect an extent or degree of efficacy of the thermal neuromodulation. For example, the duration of exposure can be as short as about 5, about 10, about 15, about 20, about 25, or about 30 seconds, or could be longer, such as about 1 minute, or even longer, such as about 2 minutes. Additionally or alternatively, the exposure can be intermittent or continuous to achieve the desired result.

The energy delivery device 110 includes a catheter-mounted balloon 116 including an inflatable chamber 117 and an electrode 118 disposed on inflatable chamber 117. The catheter-mounted balloon 116 is disposed on an elongate member 128, which is a catheter. Inflatable chamber 117 defines irrigation apertures 138 and is, in some embodiments, an inflatable balloon.

Catheter-mounted balloon 116 is delivered intravascularly via a guide catheter (not shown) and along a guidewire 140 in a folded configuration and is then inflated by flowing fluid (e.g., saline solution) to raise the pressure in inflatable chamber 117 and cause inflatable chamber 117 and electrode 118 to unfold. Inflatable chamber 117 may be made of non-elastic/non-compliant material or of compliant/elastic. Materials for a non-compliant inflatable chamber 117 include, without limitation, polyethylene, polyethylene terephthalate, polypropylene, cross-linked polyethylene, polyurethane, and polyimide. Materials for a compliant inflatable chamber 117 include, without limitation, nylon, silicon, latex, and polyurethane.

Inflatable chamber 117 can be any suitable size. In some embodiments, the diameter (e.g., a diameter of a cylindrical body portion) of inflatable chamber 117 is about 4 mm to about 10 mm. In certain embodiments, the inflatable chamber 117 has a diameter (e.g., a diameter of a cylindrical body portion) of about 5 mm, about 6 mm, or about 7 mm. The axial length of the inflatable chamber 117 can range from about 10 mm to about 50 mm. In some embodiments, the axial length of the inflatable chamber 117 is about 15 mm to about 30 mm. In some embodiments, the length of the inflatable element is about 20 mm. In certain embodiments, the axial length of the cylindrical intermediate portion of inflatable chamber 117 is between about 1 cm and about 4 cm. In some embodiments, the axial length of the cylindrical intermediate portion of the inflatable chamber 117 is about 20 mm and the diameter is about 5 mm to about 7 mm.

The electrode 118 (e.g., a single helical electrode) is disposed on inflatable chamber 117 such that inflatable chamber 117 serves as a substrate for electrode 118. In some embodiments, electrode 118 includes a helical section that makes about 0.5 revolutions to about 1.5 revolutions around inflatable chamber 117. Electrode 118 can be formed, for example, by depositing a conductive material on the exterior wall of the inflatable chamber 117, following depositing an insulation material on sections of the inflatable chamber 117, leaving electrode 118 as the only substantially conductive surface on the portion of the catheter-mounted balloon 116 that is expected to come into contact with tissue.

In some embodiments, portions of electrode 118 are covered by insulation material, forming a plurality of discrete conductive sections on electrode 118. In such embodiments, a single conductor can be used to create a number of discrete burn zones following a helical path along and around a vessel wall. In use, these embodiments create a discontinuous helical burn pattern formed by a plurality of discrete burn areas in the tissue. The helical burn pattern can be formed during a single treatment session, and does not require the device be moved to create the plurality of discrete burn areas. Applicants have previously described mechanisms for generating various electrode patterns for use in renal neuromodulation in commonly owned and co-pending PCT/US2012/057967, filed on Sep. 28, 2012, which has been incorporated herein by reference in its entirety. Other electrodes (including probe-mounted electrodes) located within or outside of inflatable chamber 117 can additionally or alternatively be used.

Irrigation apertures 138 include one or more holes (which may have any suitable size or shape) for providing protective irrigation to non-target tissue and/or cooling the electrode(s) in connection with renal neuromodulation. Irrigation apertures 138 can be defined along any suitable location on the inflatable chamber 117, such as along the contours of and outside of electrode 118, within the electrode(s) 118, or elsewhere on inflatable chamber 117.

The system 100 can include a fluid reservoir (not shown) in fluid communication with the energy delivery device 110 via an irrigation line. Irrigation fluid from the fluid reservoir is delivered by a pump integrated with the energy generator 120, and controlled by the same, to the energy delivery device 110 through an irrigation line. The irrigation fluid then flows out of the inflatable chamber 117 through the irrigation apertures 138. The energy generator 120 controls operation of the pump to control the flow rate of the fluid from the reservoir into the inflatable chamber 117. In some embodiments, the pump continuously pumps at a constant flow rate such that the flow is continuous from the reservoir. In certain embodiments, the pump is operated in an open loop constant flow configuration in which the pump rate is controlled by an over-pressure condition sensed by a pressure sensor (not shown), in which case the energy delivery is terminated, the pump is turned off, and an over-pressure condition reported to the operator. The pump is typically operated for a period of time which encompasses the delivery of the energy and turned off shortly after the conclusion of the procedure or if the pressure sensor senses an undesirable condition, as discussed in further detail below.

The pressure sensor measures the operating pressure within inflatable chamber 117, and may be adapted to determine if the pressure rises above or below threshold limits. The pressure can elevate if, for example, one or more of irrigation apertures 138 become blocked, preventing fluid from passing out of inflation chamber 117, which can reduce cooling of electrode 118. The memory of energy generator 120 can include computer-executable instructions, executable by control circuitry of energy generator 120, to suspend (e.g., pause or terminate) delivery of energy to electrode 118, and to shut off the fluid pump if the fluid pressure rises above an established limit. In some embodiments, the pressure measured at the pressure sensor is driven by the fluid flow rate and the series sum of the fluid resistance of all of the elements in the fluid path. The choice of fluid flow rate may be affected by the required cooling rate and by the amount of irrigant fluid that can be tolerated by the patient.

The operating pressure within inflatable chamber 117 may be affected by the fluid flow, the number of apertures 138, and cross sections of irrigation apertures 138. The distribution, number, and cross section of irrigation apertures 138 will be a function of the flow rate of irrigation fluid provided by the pump of energy generator 120, the configuration of electrode 118, the intended operating pressure, and the maximum desired exit velocity for the irrigation fluid at the treatment site.

Device 110 can include at least one marker 127 disposed on catheter shaft 128 such that the marker is within inflatable chamber 117. In some embodiments, marker 127 is a radio opaque marker (e.g., a marker including one or more of platinum and platinum-iridium). In certain embodiments, marker 127 also includes features viewable under fluoroscopy that allow, for example, for visualization of rotational orientation of marker 127. This can facilitate location and/or realignment of the inflatable chamber 117 and electrode 118 by the operator within the renal artery.

Figure 12B:
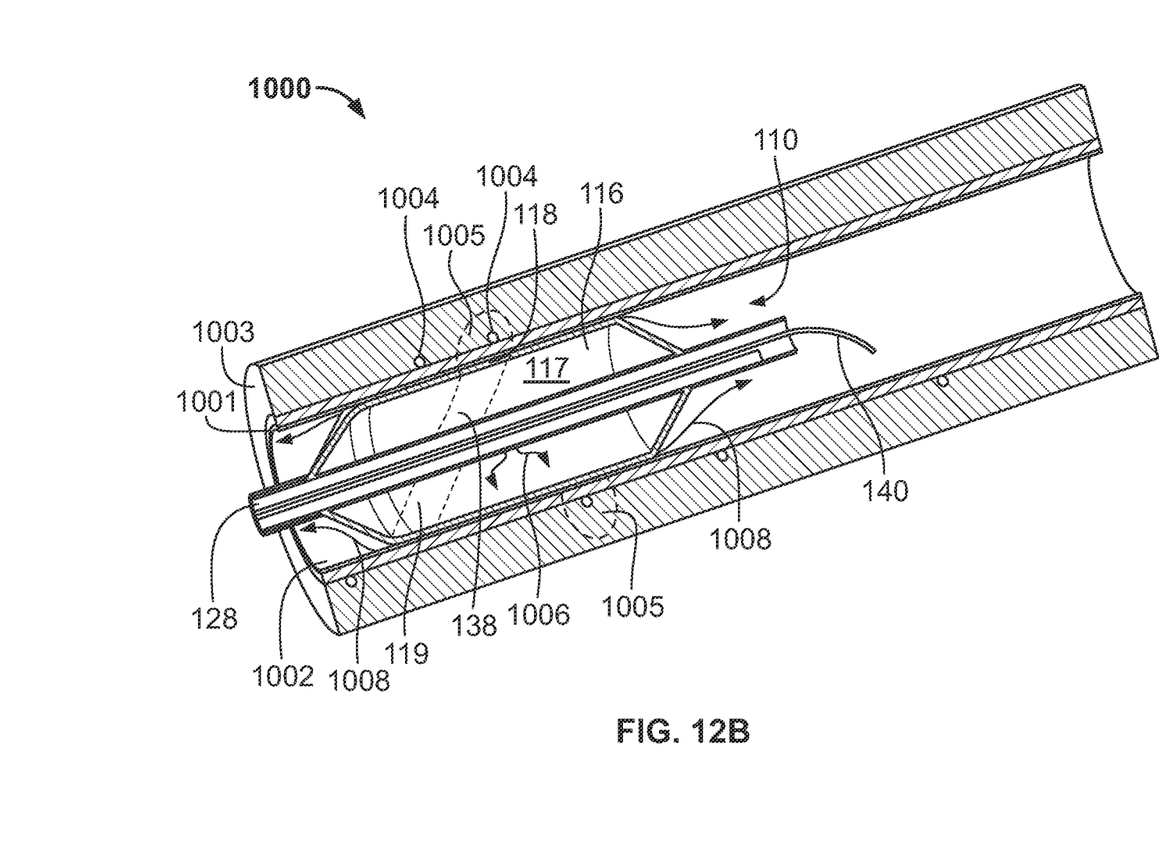
FIG. 12B illustrates an energy delivery device in use within a renal artery according to some embodiments.

Referring to FIG. 12B, an exemplary method is shown for using system 100 for a renal denervation procedure by application of RF energy to tissue in a renal artery. The method described herein can be carried out by other systems and by other energy-delivery devices, such as the other devices described herein. The energy-delivery device 110 is positioned in a renal artery using percutaneous access through a femoral artery. The inflatable element is delivered into the renal artery 1000 in a collapsed configuration (not shown). Fluid from the fluid reservoir is pumped (e.g., in an open loop control configuration, under constant flow) through the irrigation line and into the inflatable chamber 117 by the pump controlled by the energy generator 120 (FIG. 12A). Fluid flow inflatable chamber 117 causes inflatable chamber 117 to expand. Device 110 in FIG. 12B is in a delivered, or expanded, configuration within renal artery 1000. The tunica intima 1001 is surrounded by the tunica media 1002, which is in turn surrounded by adventitial tissue 1003. Tissue renal nerves 1004 are shown within the adventitial, and some renal nerves (not shown) are located within the tunica media.

The fluid continually passes through apertures 138 in the inflatable chamber 117 as the fluid is replaced with new fluid from the fluid reservoir. Once fully expanded, electrode 118 on inflatable chamber 117 assumes a helical configuration as shown in FIG. 12A. RF energy is delivered to electrode 118 on the inflatable chamber 117. Energy generator 120 controls the parameters of the RF energy being delivered to the electrode 118 via conductive material carried by the catheter shaft 128. In general, the RF signal characteristics are chosen to apply energy to depths at which the renal nerves are disposed to ablate the renal nerves. In general, the power is selected to ablate a majority of the renal nerves adjacent to where the device is positioned within the renal nerve. In some embodiments the tissue is ablated to a depth of between about 3 mm to about 7 mm from the tissue closest to the device in the renal artery.

Tissue treated by the RF energy via the helical electrode is shown as regions 1005, delineated by a dashed line. As illustrated, a region of treated tissue 1005 adjacent to the conductor 118 includes nerve 1004. The device can be used in monopolar mode with a return electrode positioned somewhere on the patient's skin. However, it can also be used in bipolar mode without deviating from the scope of the disclosure.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A catheter-mounted balloon comprising:
   an inflatable chamber configured to expand from a deflated state to an inflated state, the inflatable chamber having a distal transition portion, a proximal transition portion, and a cylindrical body portion disposed between the distal transition portion and the proximal transition portion,
   wherein the cylindrical body portion includes at least first and second pleat zones each having a pleat that causes the inflatable chamber to collapse or fold along the pleat into a pre-determined pleat pattern when the inflatable chamber is pushed through or pulled back into a guide catheter, wherein at least a portion of each pleat extends along a longitudinal axis of the cylindrical body portion when the inflatable chamber is in the deflated state, and wherein each pleat extends at least partially into the proximal transition portion of the inflatable chamber,
   wherein the proximal transition portion includes a transition portion pleat disposed between the pleats of the first and second pleat zones, wherein the transition portion pleat extends between proximal and distal ends of the proximal transition portion substantially free of extension into the cylindrical body portion.

2. The catheter-mounted balloon of claim 1, wherein at least one of the pleats is a soft pleat.

3. The catheter-mounted balloon of claim 1, wherein at least one of the pleats is spiral around the longitudinal axis of the cylindrical body portion when the inflatable chamber is in the deflated state.

4. The catheter-mounted balloon of claim 1, wherein at least one of the pleats has a substantially zig-zag pattern along the longitudinal axis of the cylindrical body portion when the inflatable chamber is in the deflated state.

5. The catheter-mounted balloon of claim 1, wherein the inflatable chamber is collapsible along the pleats in response to a decrease in a volume of the inflatable chamber as the inflatable chamber is deflated from the inflated state to the deflated state.

6. The catheter-mounted balloon of claim 1, wherein the inflatable chamber defines at least one irrigation aperture configured to allow fluid to flow from within the inflatable chamber to outside the inflatable chamber when the inflatable chamber is in the inflated state.

7. The catheter-mounted balloon of claim 6, wherein the at least one irrigation aperture is at least partially unobstructed by the pleats when the inflatable chamber is in the deflated state.

8. The catheter-mounted balloon of claim 1, further comprising at least one electrode on a wall of the inflatable chamber.

9. The catheter-mounted balloon of claim 8, wherein at least one of the pleats traverses the at least one electrode such that the at least one electrode is pleated.

10. The catheter-mounted balloon of claim 8, wherein the pleats do not cross the at least one electrode such that the electrode is not pleated.

11. The catheter-mounted balloon of claim 8, wherein the at least one electrode comprises a plurality of electrodes.

12. The catheter-mounted balloon of claim 8, wherein the inflatable chamber defines at least one irrigation aperture configured to allow fluid to flow from within the inflatable chamber to outside the inflatable chamber when the inflatable chamber is in the inflated state, and wherein the at least one irrigation aperture is disposed between one of the pleats and a side of the at least one electrode.

13. The catheter-mounted balloon of claim 8, wherein the pleats have crinkled pleats configured to reduce a likelihood that electrical properties of the at least one electrode are compromised by the pleats.

14. The catheter-mounted balloon of claim 1, wherein the inflatable chamber comprises a layer of shape memory material.

15. The catheter-mounted balloon of claim 14, wherein the shape memory material comprises a shape-memory polymer.

16. The catheter-mounted balloon of claim 15, wherein the shape-memory polymer comprises at least one of a polyurethane-based shape memory polymer or a polyether foam.

17. The catheter-mounted balloon of claim 1, wherein at least one of the distal transition portion or the proximal transition portion of the inflatable chamber is frustoconically shaped.

18. The catheter-mounted balloon of claim 1, wherein the cylindrical body portion comprises the first pleat zone, the second pleat zone, and a third pleat zone each having a pleat that causes the inflatable chamber to collapse or fold along the pleat into the pre-determined pleat pattern when the inflatable chamber is pushed through or pulled back into the guide catheter.

19. A catheter comprising:
   a balloon at a distal portion of the catheter, wherein the balloon comprises an inflatable chamber defining a volume expandable from a deflated state to an inflated state, the inflatable chamber having a distal transition portion, a proximal transition portion, and a cylindrical body portion disposed between the distal transition portion and the proximal transition portion,
   wherein the cylindrical body portion includes a pleat zone having pleats that causes the inflatable chamber to collapse or fold along the pleats into a pre-determined pleat pattern when the inflatable chamber is pushed through or pulled back into a guide catheter, wherein at least a portion of the pleats extend along a longitudinal axis of the cylindrical body portion when the inflatable chamber is in the deflated state, wherein the pleats extend at least partially into the proximal transition portion of the inflatable chamber,
   wherein the proximal transition portion includes a transition portion pleat disposed between the pleats of the pleat zone, wherein the transition portion pleat extends between proximal and distal ends of the proximal transition portion substantially free of extension into the cylindrical body portion,
   wherein the balloon is configured for guidewire delivery to an intravascular treatment site within a blood vessel of a human patient while the inflatable chamber is in the deflated state, and wherein, when the inflatable chamber is in the inflated state, the cylindrical body portion including the pleat zone has a consistent diameter between the proximal transition portion and the distal transition portion.

20. The catheter of claim 19, wherein at least one of the pleats is a soft pleat.

21. The catheter of claim 19, wherein at least one of the pleats is spiral around the longitudinal axis of the cylindrical body portion when the inflatable chamber is in the deflated state.

22. The catheter of claim 19, wherein at least one of the pleats is a substantially zig-zag pattern along the longitudinal axis of the cylindrical body portion when the inflatable chamber is in the deflated state.

23. The catheter of claim 19, further comprising an electrode disposed along a wall of the inflatable chamber.

24. The catheter of claim 23, wherein the pleats flank both sides of the electrode.

25. The catheter of claim 23, wherein, in the inflated state, the inflatable chamber is configured to position the electrode in contact with an inner wall of the blood vessel.

26. The catheter of claim 19, wherein the inflatable chamber of the balloon comprises a layer of shape memory material.

\* \* \* \* \*